United States Patent [19]

Sloboda

[11] 4,167,580
[45] Sep. 11, 1979

[54] COMPOSITIONS AND METHOD OF USE TO TREAT ARTHRITIC DISEASE WITH M-FLUOROBENZIMIDOYLACETONITRILE

[75] Inventor: Adolph E. Sloboda, New City, N.Y.

[73] Assignee: American Cyanamid Company, Stamford, Conn.

[21] Appl. No.: 942,088

[22] Filed: Sep. 13, 1978

Related U.S. Application Data

[60] Division of Ser. No. 853,942, Nov. 22, 1977, Pat. No. 4,134,990, which is a continuation-in-part of Ser. No. 814,604, Jul. 11, 1977, abandoned, which is a continuation-in-part of Ser. No. 757,280, Jan. 6, 1977, abandoned, which is a continuation-in-part of Ser. No. 664,470, Mar. 8, 1976, abandoned.

[51] Int. Cl.$^2$ .................. A61K 31/275; C07C 121/68
[52] U.S. Cl. ................................ 424/304; 260/465E
[58] Field of Search .................. 424/304; 260/465 E

[56] References Cited

PUBLICATIONS

Lang, et al., J. Med. Chem 18, 441 (1975).

Primary Examiner—Stanley J. Friedman
Attorney, Agent, or Firm—Edward A. Conroy, Jr.

[57] ABSTRACT

This disclosure describes compositions of matter useful as anti-inflammatory agents and as inhibitors of the progressive joint deterioration characteristic of arthritic disease, and the methods of meliorating inflammation and of inhibiting joint deterioration in mammals therewith, the active ingredients of said compositions of matter being benzimidoylacetonitrile, meta-fluorobenzimidoylacetonitrile, para-fluorobenzimidoylacetonitrile, or mixtures thereof.

5 Claims, No Drawings

COMPOSITIONS AND METHOD OF USE TO TREAT ARTHRITIC DISEASE WITH M-FLUOROBENZIMIDOYLACETONITRILE

CROSS REFERENCE TO RELATED APPLICATION

This application is a division of my copending application Ser. No. 853,942, filed Nov. 22, 1977 now U.S. Pat. No. 4,134,990, which is a continuation-in-part of my abandoned application Ser. No. 814,604, filed July 11, 1977, which in turn is a continuation-in-part of my abandoned application Ser. No. 757,280, filed Jan. 6, 1977 which in turn is a continuation-in-part of my abandoned application Ser. No. 664,470, filed Mar. 8, 1976.

BRIEF SUMMARY OF THE INVENTION

This invention relates to novel compositions of matter useful as anti-inflammatory agents and as inhibitors of the progressive joint deterioration characteristic of arthritic disease. More particularly, it relates to therapeutic compositions containing benzimidoylacetonitrile, m-fluorobenzimidoylacetonitrile or p-fluorobenzimidoylacetonitrile (or mixtures thereof in any proportion) which meliorate inflammation and inhibit arthritic joint deterioration in mammals. The active ingredients of the present invention and their tautomeric forms may be represented by the following structural formulae:

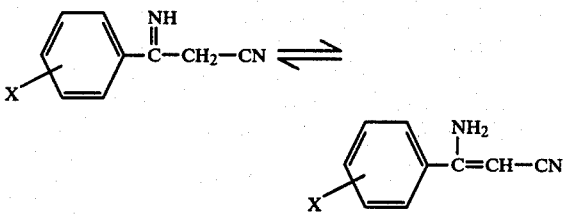

wherein X is hydrogen, m-fluoro or p-fluoro. Benzimidoylacetonitrile and p-fluorobenzimidoylacetonitrile have been described by Lange et al., J. Med. Chem. 18, 441 (1975) and benzimidoylacetonitrile may be readily prepared by the method of Iwai et al., Chem. Pharm. Bull. (Tokyo) 12, 1446 (1946). This compound is also commercially available from the Aldrich Chemical Co. of Milwaukee, Wisconsin, under the name $\beta$-iminohydrocinnamonitrile.

DETAILED DESCRIPTION OF THE INVENTION

Benzimidoylacetonitrile, m-fluorobenzimidoylacetonitrile and p-fluorobenzimidoylacetonitrile have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredients may be administered in any convenient manner such as by the oral, intravenous, intramuscular, topical, intra-articular or subcutaneous routes.

Compositions according to the present invention having the desired clarity, stability and adaptability for parenteral and intra-articular use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed by from about 3.0 to about 9.0% by weight. Although various mixtures of the aforementioned non-volatile polyethylene glycols may be employed, it is preferred to use a mixture having an average molecular weight of from about 200 to about 400.

In addition to the active compounds, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-$\alpha$-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.05 mg./ml. of the finished compositions. They are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory. For intra-articular use for large joints such as the knee, from about two to about 20 mg. per joint per week may be used, with proportionally smaller doses for smaller joints.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the compounds may be incorporated with excipients and used in the form of tablets, troches, capsules, elixirs, suspensions, syrups, wafers, and the like. Such compositions and preparation should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as fatty oil. Various other materials may be present as coatings or to otherwise modify the physical form of the dosage unit. For instance, tablets, pills or capsules may be coated with shellac, sugar or both. A syrup or elixir may contain the active compounds, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

In determining the acute anti-inflammatory activity of benzimidoylacetonitrile, Royal Hart, Wistar strain rats ranging in weight from 80 to 90 grams were used. The rats were fasted overnight prior to dosing but had free access to water. The compound was administered in aqueous suspension, by gavage, in a volume of 1.7 ml. per 50 grams of rat [corresponds by hydration volume used by Winter et al., Proc. Soc. Exp. Bio. & Med. 111, 544–547 (1962)]. The phlogistic agent used was carrageenin prepared as a sterile 1% suspension in 0.9% aqueous sodium chloride for routine testing. A volume of 0.05 ml. was injected through a 26 gauge needle into the planter tissue of the right hind paw. Measurements were made 5 hours after drug administration (4 hours after carrageenin challenge). Volumes of both the normal and carrageenin inflamed feet were determined. The difference between the two measurements is considered to be the increased edema due to the carrageenin administration. Results are expressed as a C/T efficacy ratio (edema of control animals/edema of treated animals) and C/T ratio of greater than 1.41% is considered as active. Table I records the results of this test at the indicated dose levels of benzimidoylacetonitrile in comparison with known anti-inflammatory agents.

TABLE I

| The Effect of Anti-inflammatory Agents on Carrageenin Induced Edema of the Rat Paw | | | |
|---|---|---|---|
| Compound | Dose mg./kg. of body Weight | No. of Rats | C/T Edema Ratio |
| Controls | — | 64 | — |
| Benzimidoyl-acetonitrile | 250 | 8 | 2.2 |
| Aspirin | 250 | 32 | 2.8 |
| Phenyl-butazone | 250 | 32 | 2.3 |
| Indomethacin | 25 | 32 | 2.9 |

The effect of benzimidoylacetonitrile on body temperature in yeast induced pyrexia was determined by the following procedure. Groups of three Royal Hart, Wistar strain rats weighing 80±5 grams were injected subcutaneously in the nape of the neck with 0.6 ml. of a 40% suspension of dried brewers yeast in distilled water. Test compounds were suspended in a 1.5% buffered starch solution and administered at a dose of 250 mg./kg., by gavage 17 hours after challenge. Control rats were treated in a similar manner but received only the buffered starch solutions. At 19 hours post challenge the rectal temperature of each rat was measured with an electric thermometer. Each dose response experiment was replicated one or more times. Table II records the results of this test comparing benzimidoylacetonitrile with known anti-inflammatory agents.

TABLE II

| The Effect of Test Drugs on the Body Temperature of Pyretic Rats | | | |
|---|---|---|---|
| | Dose mg./kg. of body weight | Rats With Yeast Induced Pyresis | |
| Compound | | Number | Decrease In Body Temp. °C. |
| Control | — | 156 | 0 |
| Benzimidoyl-acetonitrile | 250 | 6 | 1.4* |
| Aspirin | 250 | 15 | 1.5* |
| Phenylbutazone | 250 | 15 | 1.5* |
| Indomethacin | 250 | 21 | 2.5* |

*Significantly lower temperature than pyretic controls.

Adjuvant induced experimental polyarthritis is a specific systemic disease of the rat which shares interesting similarities with rheumatoid arthritis. Specifically, the histology of the two diseases bears a remarkable resemblance as shown by C. M. Pearson et al., Am. J. Pathol. 42, 73 (1963). E. M. Glenn, Am. J. Vet. Res. 27 (116), 339 (1966) has classified adjuvant induced polyarthritis as a crippling and permanent deformity resulting from diffuse connective tissue involvement around certain susceptible joints in the rat. Zahiri et al., Can. Med. Ass. J. 101, 269 (1969) have shown that the fusiform swelling of the distal joints is associated with edema, congestion and synovitis including pannus formation, all of which precede the ultimate destruction of bone and cartilage. Furthermore, Zahiri et al. indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration. See S. Wong et al., J. Pharm. & Exptl. Ther. 185, 127 (1973) and G. R. Bobalick et al., Agents & Actions 4, 364 (1974). In a similar manner, inhibition of the progress of arthritis in paws of rats treated with the compounds of this invention also lessens associated joint deterioration.

The following test shows the activity of benzimidolylacetonitrile, m-fluorobenzimidoylacetonitrile and p-fluorobenzimidoylacetonitrile against chronic inflammation in adjuvent induced arthritis which is accompanied by joint destruction. Groups of three Royal Hart, Wistar strain rats weighing 200±10 grams each were injected intradermally in in the right hind paw with Freund's adjuvant (dried human tubercle bacilli in a mineral oil vehicle) at a dose of 2 mg./kg. of body weight. Test compounds were administered orally in a 1.5% staruh vehicle at various doses once daily on days 0 through 13 post challenge. Control rats were treated in a similar manner, but given only starch vehicle. On the 14th and 21st day post challenge the diameter of the injected paw (primary lesion) was measured by micrometer caliper. The volume of inflamed paws were estimated from these measurements and the results are expressed as percent inhibition of swelling as compared to controls. At the same time, the other inflamed sites, such as ears, paws and tail (secondary lesions) were observed and each rat was graded as to degree of inflammation and swelling present. The grading is based on a scale of 0 to 24, where 0 represents a complete absence of induced arthritic nodules and 24 represents the maximum degree of inflammation. The mean grade for each treated group is calculated and the effects of each compound are expressed as percent inhibition of the control grade. Table III records the results of these tests conducted with benzimidoylacetonitrile, m-fluorobenzimidoylacetonitrile and p-fluorobenzimidoylacetonitrile and known anti-inflammatory agents. The active compounds of the present invention suppress the progression of the arthritis and associated joint deterioration. Of particular interest is the low mortality observed with benzimidoylacetonitrile treated rats relative to either controls or rats treated with standard compounds. Benzimidoylacetonitrile also appears to have a longer duration of action than standards as shown by the greater suppression of primary and secondary lesions at the 21 day observation period.

Another method of determining a drug effect on conditions which result in inflammation is be measuring the effect on ultraviolet induced erythema in guinea pigs. Albino guinea pigs were depilated on their flanks, the evening before testing, with a standard mixture of barium sulfide and gum acacia. On the morning of the test at 0 hour they were restrained in a plastic container which allows exposure of 3 circular spots. They were then exposed to ultraviolet irradiation from a "Hanovia" Kromayer lamp, model 10, for 60 seconds. Immediately after exposure to ultraviolet light, the guinea pigs were treated by dissolving the test compound in ethyl alcohol at various concentrations and swabbing the UV exposed areas with the aid of a cottom tipped applicator stick. At one and four hours, the degree of erythema for each of the three sites was assessed according to the following scoring system: 0=no erythema, 0.5=incomplete circle or faint erythema and 1.0=complete circle of distinct erythema. Thus, the maximum score for each animal was 3.0. The following Table IV summarizes the results of this test with benzimidoylacetonitrile and other drugs known to have a beneficial effect in erythema in warm-blooded animals.

TABLE III

The Effect of Anti-inflammatory Agents on Adjuvant Arthritis in Rats

| Compound | Oval Dose mg./kg. of body weight | Dead/Treated At 21 Days | Mean Weight Gain (grams) | | % Inhibition of Swelling (primary lesion) | | % Inhibition of Control Grade (secondary lesion) | |
|---|---|---|---|---|---|---|---|---|
| | | | Day 14 | Day 21 | Day 14 | Day 21 | Day 14 | Day 21 |
| Normal Rats | — | 8/186 | 77 | 112 | — | — | — | — |
| Adjuvant Controls | — | 53/630 | 36 | 31 | 0 | 0 | 0 | 0 |
| Indomethacin | 2 | 8/57 | 68* | 68* | 51* | 24* | 38* | 25* |
| | 1 | 9/54 | 63* | 65* | 46* | 19* | 34* | 20* |
| | 0.5 | 5/54 | 53* | 51* | 40* | 20* | 25* | 17* |
| | 0.25 | 0/9 | 51 | 57* | 30* | 4 | 22* | 4 |
| Aspirin | 400 | 19/57 | 41 | 55* | 73* | 48* | 58* | 45* |
| | 200 | 10/66 | 40 | 44 | 48* | 27* | 26* | 17* |
| | 100 | 18/63 | 48 | 53* | 36* | 13 | 19* | 8 |
| | 50 | 2/21 | 56* | 44 | 23* | 3 | 12 | 9 |
| Phenylbuta- | 150 | 2/27 | 40 | 50* | 75* | 44* | 54* | 31* |
| zone | 75 | 2/39 | 51* | 50* | 62* | 28* | 27* | 15 |
| | 37.5 | 5/39 | 53* | 53* | 56* | 14 | 18 | 13 |
| | 18.8 | 2/21 | 50* | 45 | 31 | 7 | 4 | 8 |
| Benzimidoyl- | 100 | 0/15 | 46 | 65* | 68* | 60* | 57* | 46* |
| acetonitrile | 50 | 1/24 | 31 | 49* | 63* | 62* | 59* | 48* |
| | 25 | 1/9 | 41 | 38 | 33* | 32* | 33* | 16* |
| P-Fluorobenz- | 100 | 1/18 | 78* | 67* | 53* | 29* | 49* | 22* |
| imidoylaceto- | 50 | 4/36 | 66* | 57* | 43* | 25* | 27* | 8 |
| nitrile | 25 | 2/18 | 53 | 50 | 26 | 14 | 14 | 9 |
| m-Fluorobenz- imidoylaceto- nitrile | 50 | 1/18 | 64 | 60 | 40* | 7 | — | — |

*Significantly different from adjuvant controls.

TABLE IV

The Comparative Effect of Topically Applied Anti-inflammatory Agents on Development of Erythema in Guinea Pigs (pooled data)

| Vehicle For Topical Application | Drug | % Concentration of Drug In Vehicle | Number of Animals | Score (Avg.) 1 Hr. | 4 Hr. |
|---|---|---|---|---|---|
| Ethyl Alcohol | Control | — | 40 | 2.5 | 3.0 |
| | Indomethacin | 1 | 16 | 0.7* | 2.5 |
| | | 0.5 | 8 | 1.5 | 2.4 |
| | | 0.25 | 8 | 1.8 | 2.5 |
| | Aspirin | 1 | 4 | 1.9 | 2.8 |
| | Phenylbutazone | 1 | 8 | 0.5* | 2.4 |
| | Benzimidoylacetonitrile | 2 | 8 | 0.6* | 2.7 |
| | | 1 | 4 | 1.0 | 2.8 |

*Statistically significant activity.

The invention will be described in greater detail in conjunction with the following specific examples.

EXAMPLE 1

| Preparation of 50 mg. Tablets | | |
|---|---|---|
| Per Tablet | | Per 10,000 Tablets |
| 0.050 gm. | Benzimidoylacetonitrile | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The benzimidoylacetonitrile, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 2

| Preparation of Oral Syrup | |
|---|---|
| Ingredient | Amount |
| p-Fluorobenzimidoylacetonitrile | 500 mg. |
| Sorbitol Solution (70% N.F.) | 40 ml. |
| Sodium benzoate | 150 mg. |
| Saccharin | 10 mg. |
| Red dye | 10 mg. |
| Cherry flavor | 50 mg. |
| Distilled water    qs   ad | 100 mg. |

The sorbitol solution is added to 40 ml. of distilled water and the p-fluorobenzimidoylacetonitrile is suspended therein. The saccharin, sodium benzoate, flavor and dye are added and dissolved. The volume is adjusted to 100 ml. with distilled water. Each ml. of syrup contains 5 mg. of p-fluorobenzimidoylacetonitrile.

EXAMPLE 3

Preparation of Parenteral Solution

In a solution of 700 ml. of propylene glycol and 200 ml. of water for injection is suspended 20.0 grams of benzimidoylacetonitrile with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 4

| Preparation of Topical Cream | |
|---|---|
| Ingredient | Amount |
| m-Fluorobenzimidoylacetonitrile | 1.0% |
| Ethoxylated stearyl alcohol | 10.0% |
| Benzyl alcohol | 0.9% |
| Isopropyl palmitate | 5.0% |
| Glycerin | 5.0% |
| Sorbitol solution (USP) | 5.0% |
| Lactic acid   qs. to   pH 4.0-5.0 | |

| -continued | |
|---|---|
| Preparation of Topical Cream | |
| Ingredient | Amount |
| Water   qs. to | 100.0% |

The ethoxylated stearyl alcohol and isopropyl palmitate are heated to liquifying temperature. About 95% of the total volume of water is placed in a separate container followed by the glycerin and sorbitol solution. This aqueous mixture is brought to a boil and then cooled to 60°-75° C. The m-fluorobenzimidoylacetonitrile is added to the wax phase and the mixture is stirred until a clear solution is obtained. The benzyl alcohol is added and dissolved in the wax phase while maintaining agitation. Both phases are kept at about the same temperature during transfer. The mixture is cooled while agitation is continued. At a temperature of 50°-55° C. the balance of the water is added. The pH is adjusted to 4.0-5.0 with lactic acid. The batch is cooled with minimum agitation until the cream sets in its final form.

EXAMPLE 5

| Preparation of Intra-articular Product | |
|---|---|
| Ingredient | Amount |
| Benzimidoylacetonitrile | 2-20 mg. |
| NaCl (physiological saline) | 0.9% |
| Benzyl alcohol N.F. | 0.9% |
| Sodium carboxymethylcellulose | 1-5% |
| pH adjusted to 5.0-7.5 | |
| Water for injection   qs ad | 100% |

EXAMPLE 6

| Preparation of Injectable Depo Suspension | |
|---|---|
| Ingredient | % W/V |
| Benzimidoylacetonitrile | 0.05-5.0 |
| Polysorbate 80 USP | 0.2 |
| Polyethylene glycol 4000 USP | 3.0 |
| Sodium chloride USP | 0.8 |
| Benzyl alcohol N.F. | 0.9 |
| HCl to pH 6-8 | qs |
| Water for injection   qs ad | 100.0 |

EXAMPLE 7

Preparation of m-Fluorobenzimidoylacetonitrile

A 1.21 g. portion of m-fluorobenzonitrile, 0.52 ml. of acetonitrile, 0.5 g. of sodium hydride and 0.1 ml. of t-butanol are added to 25 ml. of ether. The mixture is refluxed on a steam bath for one hour. Methanol and water are added. The layers are separated and the aqueous layer is extracted with two 25 ml. portions of ether. The combined ether layers are dried over sodium sulfate, passed through diatomaceous earth, diluted with hexanes and evaporated on a steam bath. The resulting oil is chromatographed using methylene chloride on silica gel giving 0.52 g. of an oil which crystallizes. This material is taken up in methylene chloride. Hexanes are added and the mixture is evaporated giving an oil which crystallizes. This material is recrystallized from carbon tetrachloride giving the desired product, m.p. 67°-68° C.

I claim:
1. m-Fluorobenzimidoylacetonitrile.

2. The method of inhibiting the progression of arthritis in a mammal which comprises administering to said mammal an effective amount of m-fluorobenzimidoylacetonitrile.

3. The method of inhibiting progressive joint deterioration in a mammal which comprises administering to said mammal an effective amount of m-fluorobenzimidoylacetonitrile.

4. The method of meliorating inflammation in a mammal which comprises administering to said mammal an effective amount of m-fluorobenzimidoylacetonitrile.

5. an anti-arthritic composition in dosage unit form useful for meliorating the inflammation and/or the progressive joint deterioration characteristic or arthritic disease in mammals comprising from about one milligram to about 250 milligrams per kilogram of body weight per dosage unit of m-fluorobenzimidoylacetonitrile in association with a pharmaceutical carrier.

* * * * *